US00PP37231P2

(12) United States Plant Patent
Kapias

(10) Patent No.: US PP37,231 P2
(45) Date of Patent: Jan. 27, 2026

(54) ***THUJA* PLANT NAMED 'GK01'**

(50) Latin Name: *Thuja occidentalis*
Varietal Denomination: GK01

(71) Applicant: Wojciech Kapias, Goczałkowice-Zdrój (PL)

(72) Inventor: Wojciech Kapias, Goczałkowice-Zdrój (PL)

(73) Assignee: VAN VLIET NEW PLANTS B.V., Stroe (NL)

( * ) Notice: Subject to any disclaimer, the term of this patent is extended or adjusted under 35 U.S.C. 154(b) by 0 days.

(21) Appl. No.: 19/048,908

(22) Filed: Feb. 8, 2025

(51) Int. Cl.
*A01H 5/00* (2018.01)
*A01H 6/00* (2018.01)

(52) U.S. Cl.
USPC ..... Plt./213

(58) Field of Classification Search
USPC ..... Plt./213
See application file for complete search history.

(56) References Cited

PUBLICATIONS

The Polish Nurserymen Association website. 2025. https://e-katalogroslin.pl/plants/11588,zywotnik-zachodni-great-star-gk01_thuja-occidentalis-great-star-gk01?se=12a9c2e5dcd5ec9666548a01bee7dcd5. 2 pages. (Year: 2025).*

* cited by examiner

*Primary Examiner* — Karen M Redden
(74) *Attorney, Agent, or Firm* — Penny J. Aguirre

(57) ABSTRACT

A new cultivar of *Thuja* plant named 'GK01' that is characterized by its strongly fastigiate and compact plant habit and its dark green foliage.

2 Drawing Sheets

Botanical classification: *Thuja occidentalis.*
Varietal denomination: 'GK01'.

CROSS REFERENCE TO A RELATED APPLICATION

This application is related to a European plant breeders' rights application filed on Sep. 13, 2022, application No. 2022/2070. The information for the Plant Breeders' Rights Application was received directly from the Inventor.

BACKGROUND OF THE INVENTION

The present invention relates to a new and distinct cultivar of *Thuja occidentalis* and will be referred to hereafter by its cultivar name, 'GK01'. 'GK01' represents a new cultivar of arborvitae, an evergreen tree grown for landscape use.

The Inventor discovered 'GK01' as a naturally occurring branch mutation of *Thuja* 'Smaragd' (not patented) that was growing outdoors in a container at a nursery in August of 2018 in Goczałkowice-Zdrój, Poland.

Asexual propagation of the new cultivar was first accomplished by the Inventor using stem cuttings in Goczałkowice-Zdrój, Poland in November of 2018. Asexual propagation by stem cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'GK01' as a unique cultivar of *Thuja.*

1. 'GK01' exhibits a strongly fastigiate and compact plant habit.
2. 'GK01' exhibits dark green foliage.

The parent plant of 'GK01' differs from 'GK01' in having a less compact habit, a broader width, and lighter green foliage. 'GK01' can be most closely compared to the *Thuja* cultivars 'Thucavlo' (U.S. Plant Pat. No. 31,775) and 'King of Brabant' (U.S. Plant Pat. No. 29,678). 'Thucavlo' is similar to 'GK01' in having a fastigiate and compact plant habit. 'Thucavlo' differs from 'GK01' in having lighter green foliage; especially in winter. 'King of Brabant' is similar to 'GK01' in having an upright plant habit. 'King of Brabant' differs from 'GK01' in having a less compact plant habit and lighter green foliage.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listing by Polish Nurserymen Association (introduced in a new plant competition), Grupa Kapias (Groot Groen Plus new plant competition), KVBC, Van Vliet New Plants, e-katalogroslin, Plantago, Tumbig, and Plantsearch.

BRIEF DESCRIPTION OF THE DRAWINGS

The accompanying color photographs illustrate the overall appearance and distinct characteristics of the new *Thuja*.

The photographs were taken of a 5.5-year-old plant as grown outdoors in a 37-cm container in Stroe, The Netherlands.

Figure 1:
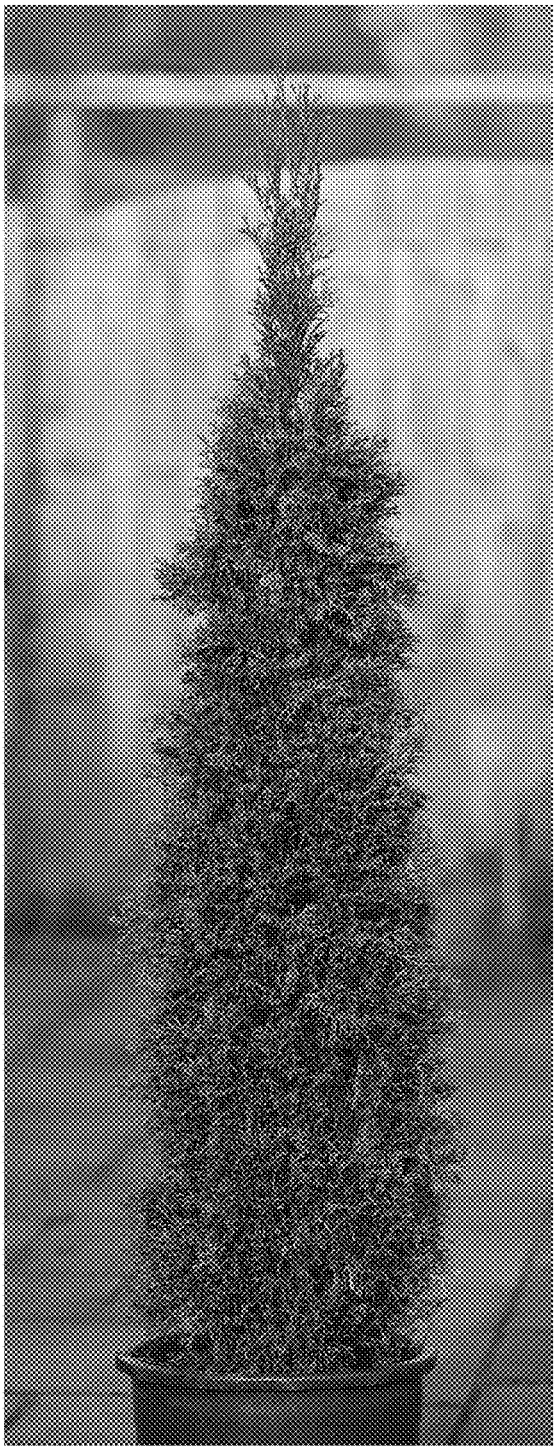

The photograph in FIG. 1 provides an overall view of the plant habit of 'GK01'.

Figure 2:
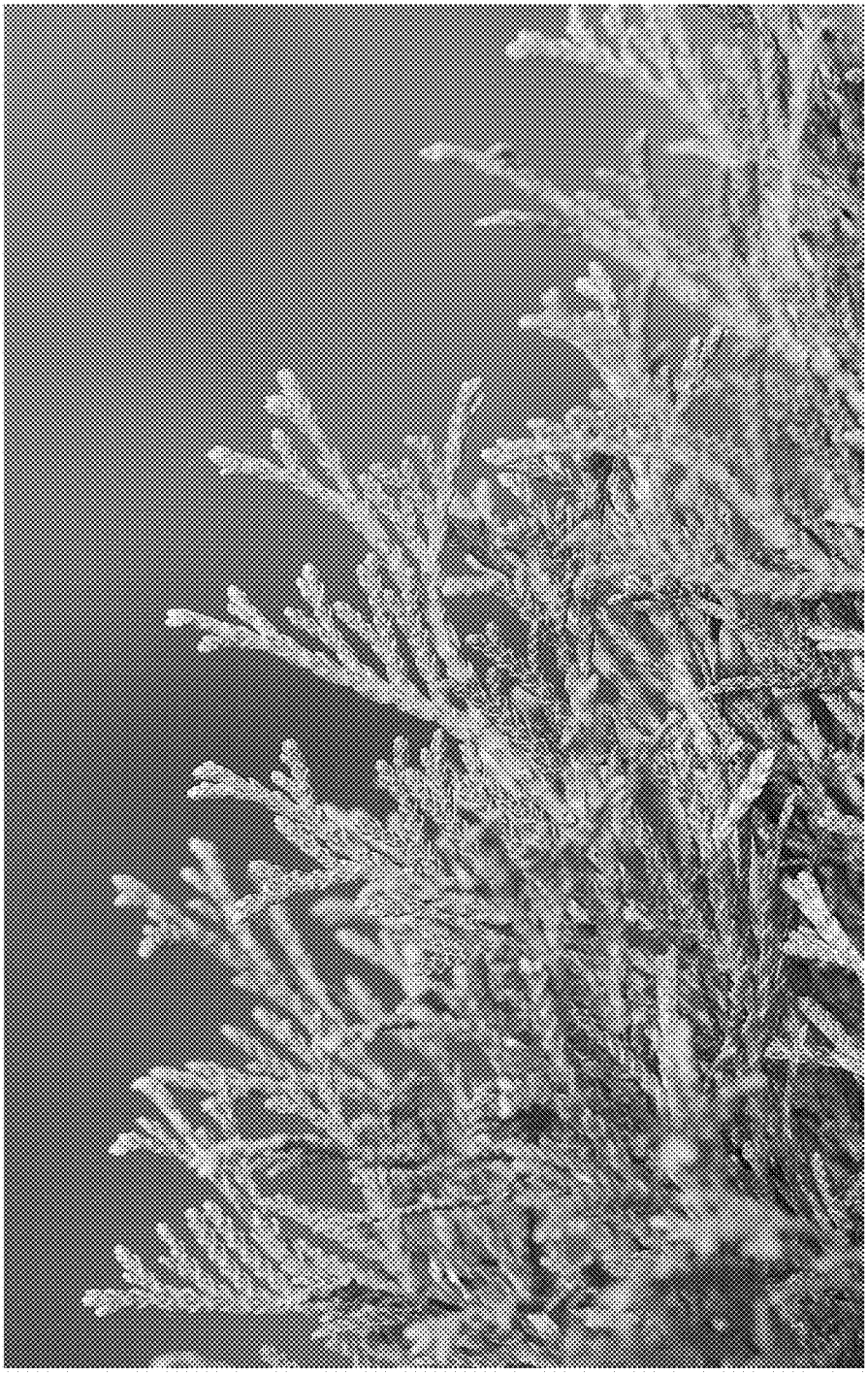

The photograph in FIG. 2 provides a close-up view of the foliage of 'GK01'.

The colors in the photographs are as close as possible with the photographic and printing technology utilized and the color values cited in the detailed botanical description accurately describe the colors of the new *Thuja*.

DETAILED BOTANICAL DESCRIPTION

The following is a detailed description of the new cultivar as taken from 5.5-year-old plants as grown outdoors in 37-cm containers in Stroe, The Netherlands. The phenotype of the new cultivar may vary with variations in environmental, climatic, and cultural conditions, as it has not been tested under all possible environmental conditions. The color determination is in accordance with the 6$^{th}$ edition, 2019 reprint Colour Chart of The Royal Horticultural Society, London, England, except where general color terms of ordinary dictionary significance are used.

General description:

*Plant type*.—Coniferous, evergreen tree.

*Plant habit*.—Narrow conical to fastigiate, dense and compact.

*Plant size*.—Reaches an average of 1.61 m in height and 43 cm in width as a 5.5 year-old plant grown in a container, reaches 2 m in height and 70 cm in width in the landscape.

*Hardiness*.—At least in U.S.D.A. Zones 3 to 11.

*Diseases and pests*.—No resistance or susceptibility to diseases or pests has been observed.

*Root description*.—Fibrous, moderately branched, moderately thick, 175A in color.

*Propagation*.—Stem cuttings.

*Growth rate*.—Moderate.

*Plant vigor*.—Moderate to high.

*Root development*.—Roots initiate in 5 months, a fully rooted young plant is produced in 12 months from a rooted cutting.

Branch description:

*Branch quantity*.—Average of 1 main branch, with an average of 45 branches per lateral branch.

*Branch shape*.—Rounded.

*Branch size*.—Average of 41.1 cm in length, 5 mm in diameter.

*Branch surface*.—Densely covered with scale-like leaves that are very slightly glossy, scale-like leaves very slightly glossy.

*Branch arrangement*.—Alternate.

*Branch strength*.—Strong.

*Internode length*.—Average of 3.2 cm.

*Branch color*.—Young branches; 144A to 144B, mature branches; 164A to 165A, older bark; 197C, N199A and N199B.

Foliage description:

*Leaf arrangement*.—Opposite.

*Leaf attachment*.—Sessile.

*Leaf shape*.—Linear, scale-like.

*Leaf division*.—Simple.

*Leaf base*.—Decurrent.

*Leaf apex*.—Apiculate to short apiculate.

*Leaf venation*.—Not distinguishable, coloration matches leaf coloration.

*Leaf margins*.—Entire.

*Leaf fragrance*.—When crushed, scale-like leaves produce a very strong pleasant smell typical fragrance of *Thuja*.

*Leaf surface*.—Upper and lower surfaces; glabrous, smooth and slightly to moderately glossy.

*Leaf color*.—Immature upper and lower surface; 148A, mature upper and lower surface; 143A and 143B.

*Leaf size*.—Average of 3 mm in length and 1.5 mm in width.

*Leaf quantity*.—Average of over 4,000 scale-like leaves per branch.

*Leaf glands*.—Average of 0.5 mm in diameter, circular in shape, 147B in color.

Cone description: Neither male nor female cones have been observed to date.

It is claimed:

1. A new and distinct cultivar of *Thuja* plant named 'GK01' as herein illustrated and described.

* * * * *